United States Patent

Mooreville et al.

Patent Number: 5,803,897
Date of Patent: Sep. 8, 1998

[54] PENILE PROTHESIS WITH PUMP ROTOR DIRECTLY ACTUATED BY ROTATING MAGNETIC FIELD

[76] Inventors: Michael Mooreville, 287 Sycamore Ave., Merion Station, Pa. 19066; Sorin Adrian, 311 Fawn Hill La., Penn Valley, Pa. 19072

[21] Appl. No.: 832,700

[22] Filed: Apr. 12, 1997

[51] Int. Cl.$^6$ .................................................. A61F 5/00
[52] U.S. Cl. .............................................................. 600/40
[58] Field of Search ........................... 600/38–41, 16–18; 128/899, 897

[56] References Cited

U.S. PATENT DOCUMENTS

| | | |
|---|---|---|
| 4,572,168 | 2/1986 | Fischell .................................... 600/40 |
| 4,584,994 | 4/1986 | Bamberger et al. ....................... 600/40 |
| 4,941,461 | 7/1990 | Fischell . | |
| 5,437,605 | 8/1995 | Helmy . | |

OTHER PUBLICATIONS

Which Patients, Which Devices For Prosthesis Implantation? D. Montague pp. 17–27 of Apr./May 1989 Issue of Contemporary Urology.
Development of a Penile Prosthesis—The Hydroflex by C. Porter, pp. 149–163 of Urology Clinics of North America, vol. 16, No. 1 Feb. 1989.

*Primary Examiner*—John P. Lacyk
*Assistant Examiner*—Samuel Gilbert
*Attorney, Agent, or Firm*—William H. Meise

[57] ABSTRACT

A penile prosthesis includes a rotary pump for pressurizing a bag or chamber within the penis. The rotary pump includes a magnetically active rotor which, in one embodiment, is located within the penis, which can be made to spin by a rotary magnetic field generator. The rotary magnetic field generator may be similar to those used in conjunction with brushless DC motors, or it may be a permanent magnet spun about an axis. In operation of one embodiment, the magnetic field generator surrounds the penis at a location near the rotor. The rotor drives an impeller or blades which pressurize fluid from a reservoir, and tends to pressurize the bag or chamber to thereby render the penis rigid. A valve arrangement prevents loss of pressure when the rotating field is removed. In one embodiment, the valve arrangement includes a spring-operated check valve in conjunction with another valve, and in another embodiment, a single centrifugally-operated valve performs the same function. Other embodiments locate the rotary pump under the skin in the retropubic region or the scrotum, at locations at which a rotary magnetic field generator can rotate the pump rotor.

5 Claims, 6 Drawing Sheets

PENILE PROTHESIS WITH PUMP ROTOR DIRECTLY ACTUATED BY ROTATING MAGNETIC FIELD

FIELD OF THE INVENTION

This invention relates to penile prostheses, and more particularly to such prostheses of the "hydraulic" type.

BACKGROUND OF THE INVENTION

There are two general kinds of penile prostheses, as described in the article Which patients, which devices for prosthesis implantation? by Drogo K Montague, published at pp 17–27 of the April/May, 1989 issue of the magazine Contemporary Urology. These two types are hydraulic and nonhydraulic. Among the hydraulic penile prostheses are the one-piece, which are implanted within the corpora cavernosa, and the multipiece, which have intracorporeal components connected by tubing to a pump-reservoir implanted in the scrotum. The multipiece prosthesis includes paired penile cylinders, a scrotal pump, and a retropubic fluid reservoir. The penile cylinder may be distensible, or it may be non-distensible, amounting to no more than a "bag," so that fluid can be pumped in at low pumping pressure, and once the cylinder is full, additional pumping pressurizes the chamber of the cylinder without expanding. The shape and length of the inflatable bag is selected to fit the penis in which it or they are to be implanted. The inflatable cylinder or bag will be termed a "chamber" herein, whatever its shape or material. For various reasons, manually operated hydraulic penile prostheses can present almost insurmountable problems to some patients. These problems may arise due to lack of dexterity, unfamiliarity with the inflating pump, especially when it is out of sight surrounded by scrotal skin, or to pain caused by pressing on the scrotal pump through unusually sensitive scrotal skin.

U.S. Pat. No. 5,437,605, issued Aug. 1, 1995 in the name of Helmy, describes a prosthesis which includes a reciprocating plunger which is alternately attracted to, and repelled from, an electromagnetic device, to pump fluid. No useful method for generating the attractive and repulsive fields is described. The prosthesis of U.S. Pat. No. 4,941,461, issued Jul. 17, 1990 in the name of Fischell, uses a transformer to couple an alternating field to a secondary winding, and the energy in the secondary winding is rectified to produce direct voltage for operating a solenoid type pump. Neither of these devices seems practical, and they may be unreliable due to the many parts in linear piston-type motion.

Improved penile prostheses are desired.

SUMMARY OF THE INVENTION

A penile prosthesis arrangement according to an aspect of the invention comprises at least one pressurizable chamber. In this context, the term "chamber" refers to an expansible or elastomeric container, or to a nondistensible bag, of whatever shape, and in whatever number. The chamber includes a fluid port by which fluid can enter and leave the chamber. The chamber is located within the penis of a patient for tending to make the penis rigid in response to fluid pressure within the chamber, and to allow the penis to be flaccid in the absence of significant fluid pressure in the chamber. The penile prosthesis arrangement also includes a fluid reservoir, which may be located in the scrotum, or preferably is located within a portion of the prosthesis, such as the root portion. A rotary pump is coupled to the reservoir and to the chamber. The rotary pump includes a magnetically responsive rotor adapted for rotation in the presence of a rotating magnetic field, coupled to an impeller arrangement for tending to pump fluid at least from the reservoir toward the chamber under the impetus of fluid pressure, to thereby pressurize the chamber in response to operation of the pump. In this context, the term "impeller" includes any conventional means for converting rotational motion into linear fluid motion. The rotational impeller or pump may be in the penis, scrotum, or in the pubis above the penis, or in general in any location close to the surface of the skin at which a rotational magnetic field can drive the pump. The penile prosthesis arrangement also includes, in one embodiment, a generally annular magnetic field generator defining a central aperture or cavity large enough to accommodate at least a portion of the penis in the state in which the chamber is pressurized. The magnetic field generator generates a rotating magnetic field within the central aperture. When the magnetic field generator is placed over the penis by placing the central aperture around the penis, as near its distal end or near its root, the magnetically responsive rotor rotates in response to the rotating magnetic field, to thereby tend to pressurize the chamber and to render the penis rigid. When the magnetically active rotor is in the scrotum or in the pubis, the magnetic field generator may not require an aperture.

The prosthesis arrangement may further include a controllable valve arrangement operable in response to motion of the rotor of the rotary pump, for tending to prevent depressurization of the chamber when the rotating magnetic field no longer acts on the rotor. The controllable valve arrangement may include a unidirectional check valve located between the rotary pump and the fluid port of the chamber.

In one embodiment of the invention, the rotor of the rotary pump is free to move axially in response to the forces generated during rotation of the rotor, and the rotary pump further includes a spring arrangement coupled to the rotor, for tending to bias the rotor in a first axial direction toward a first location, whereby, when the rotor rotates for tending to pressurize the chamber, the forces acting on the rotor tend to overcome the bias, and cause the rotor to move in a second axial direction to a second position. In this embodiment, the controllable valve arrangement comprises a mechanically actuable valve which responds to the first location of the rotor for allowing depressurization of the chamber, and which responds to the second position of the rotor to prevent depressurization of the chamber. As a result, the chamber tends to maintain pressure so long as the rotor is in the second location, and to be depressurized when the rotor is near the first location. In another embodiment, the valve arrangement comprises at least one biased centrifugal closure mounted on the rotor for rotation therewith, for assuming a first condition when the rotor is stationary, and for assuming a second condition when the rotor is rotating. The closure closes a fluid path which is hydraulically in series with the rotary pump in the first condition, and opens the fluid path which is hydraulically in series with the rotary pump in the second condition, whereby when the pump is rotating the chamber can be pressurized, and when the pump is not rotating, the chamber tends to remain pressurized.

In one embodiment of the invention, the rotating magnetic field is generated by physical rotation of permanent magnets. In another embodiment, the rotating magnetic field is generated by a control circuit in conjunction with a plurality of windings.

DESCRIPTION OF THE INVENTION

Figure 1:
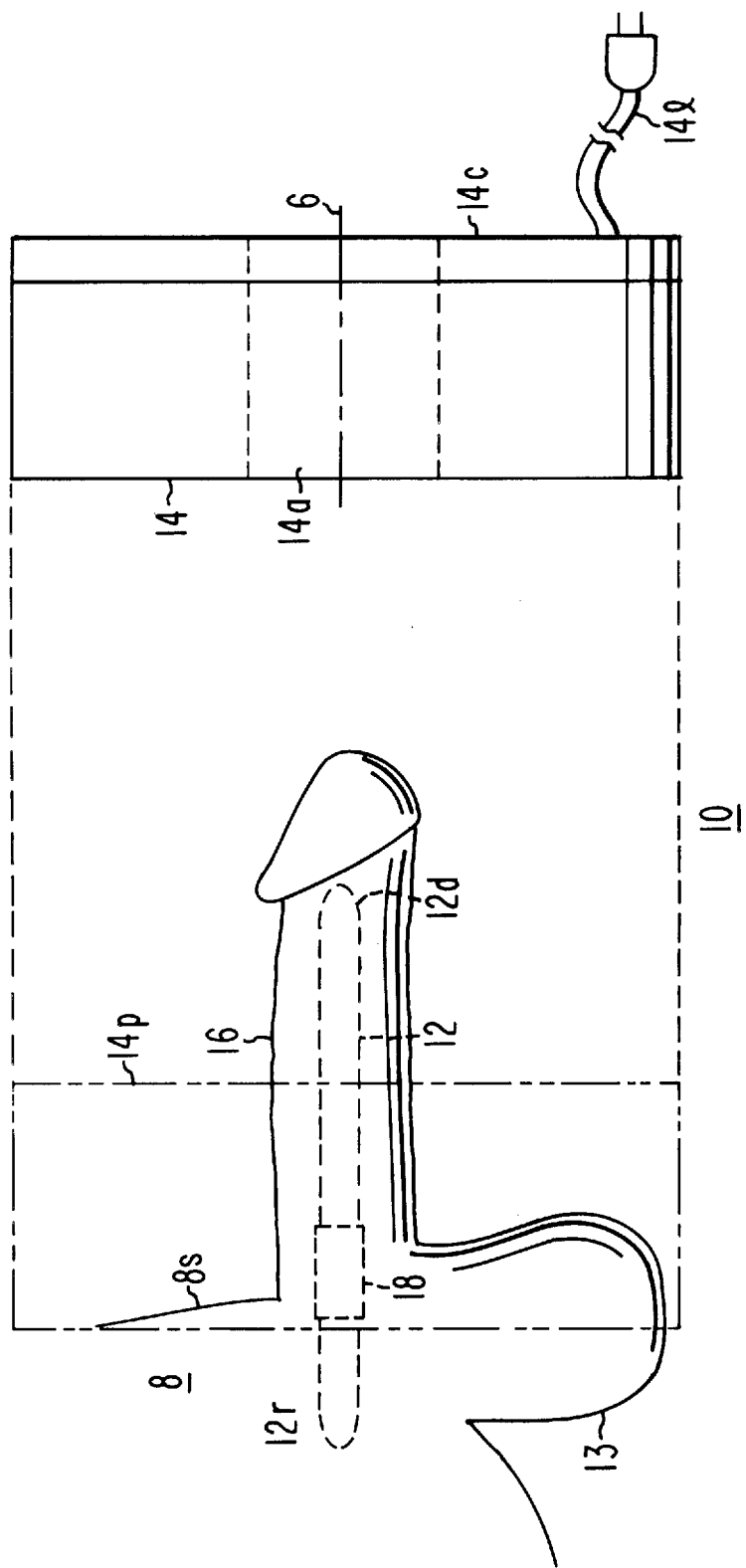
FIG. 1 is a simplified representation of a penis and a penile prosthesis arrangement including a hydraulic or pneumatic prosthesis fitted into the penis, and a separate rotary magnetic field generator.

In FIG. 1, a penile prosthesis arrangement 10 is illustrated as including an implantable prosthesis 12 and a rotary magnetic field generator 14, illustrated separated from the prosthesis 12 by solid lines. Prosthesis 12 is illustrated as being implanted in a penis 16, with a distal portion 12d of the prosthesis 12 at a distal location in the penis, and with a root portion 12r of the prosthesis near the root of the penis. Prosthesis 12 is illustrated as including a portion 18, which need not be enlarged as illustrated, which contains the pump portion of the implantable portion 12 of penile prosthesis 10. As illustrated, the pump portion 18 is somewhat forward of, or at least flush with, the outer surface 8s of the abdomen near the region of the penis 16 and of the scrotum 13.

In FIG. 1, rotary field generator 14 of penile prosthesis arrangement 10 is illustrated in solid lines separated from the penis and the implantable portion 12 of the prosthesis. Rotary field generator 14 includes a central aperture or opening 14a, which is dimensioned to accommodate the penis 16 in its tumescent condition. During inflation operation of the penile prosthesis arrangement 10, the rotary field generator 14 is placed over the penis 16, and is moved as close to the body surface 8s as possible, as suggested by phantom lines 14p. In this condition, rotary magnetic field generator 14, when energized, produces a rotating magnetic field, either by physically rotating a permanent magnet, or by controllers and windings in a manner well known to those skilled in the art of brushless direct-current (DC) rotary motors. More particularly, such rotary magnetic field generators are described, for example, in *DC MOTORS SPEED CONTROLS SERVO SYSTEMS*, The Electro-Craft Engineering Handbook, published by Reliance Motor Control, Inc., 6950 Washington Ave. South, Eden Prairie, Minn. 55344. This is accomplished, in short, by providing a number of magnetic windings spaced about the rotational axis of the field, and by energizing each winding in turn, in a predetermined sequence, from a source of electrical energy. The energization is ordinarily accomplished by solid-state switch devices, such as transistors, driven from a phase controller. The electrical controller is illustrated, in FIG. 1, as portion 14c of rotary magnetic field generator 14. Energy for operation of rotary magnetic field generator 14 may be provided by a conventional power supply, adapted to be connected by way of a line cord 141 to the alternating power lines, or more preferably by batteries associated with controller 14c.

It should be emphasized that the rotary magnetic field generator 14 of FIG. 1 generates a magnetic field which effectively rotates physically about the axis 6 of the aperture 14a. When the effective physical rotation is examined from opposite sides of generator 14, the apparent rotation will have different hands of rotation. In other words, the if the apparent physical rotation direction on one side is clockwise, it will appear to be counterclockwise if examined from the opposite side of the generator. The generation of an effectively rotating magnetic field using controller and windings is well known, and the physical rotation of a permanent magnet about an axis centered between its positive and negative poles, as in a stirrer, is also well known, and no additional description is deemed necessary. The physically rotating permanent magnet embodiment is less amenable to a central aperture, but may be better for rotating a rotor placed behind the skin of the pubis or of the scrotum.

Figure 2A:
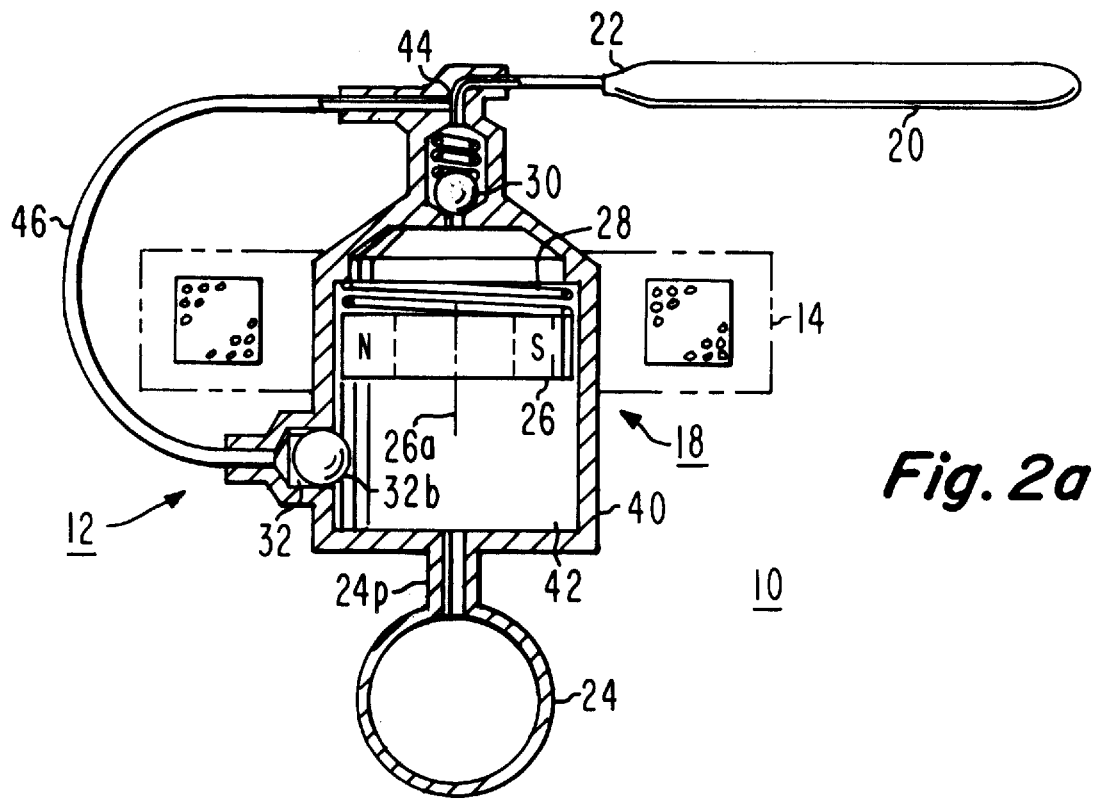
FIG. 2a is a simplified schematic diagram of the prosthesis arrangement of FIG. 1, with a rotor in a bias position.

FIG. 2a is a schematic representation of the penile prosthesis 10. In FIG. 2a, penile prosthesis 10 has a chamber or bag 20 (hereinafter chamber) which pneumatically or hydraulically is inflatable at a port 22, or pressurizable without expansion, to render the chamber relatively rigid, to thereby make the penis in which it is implanted more rigid than in the noninflated or nonpressureized condition. A fluid reservoir 24 is associated with the prosthesis 18, which may be physically located within the root portion of the prosthesis 18, or located in the scrotum 13, or within body 8 at another location. Reservoir 24 communicates with pump 18 by way of a fluid path 24p, for supplying fluid to the pump 18 during inflation or pressurization of the chamber, and for receiving fluid returned from the chamber during deflation or depressurization.

Figure 2B:
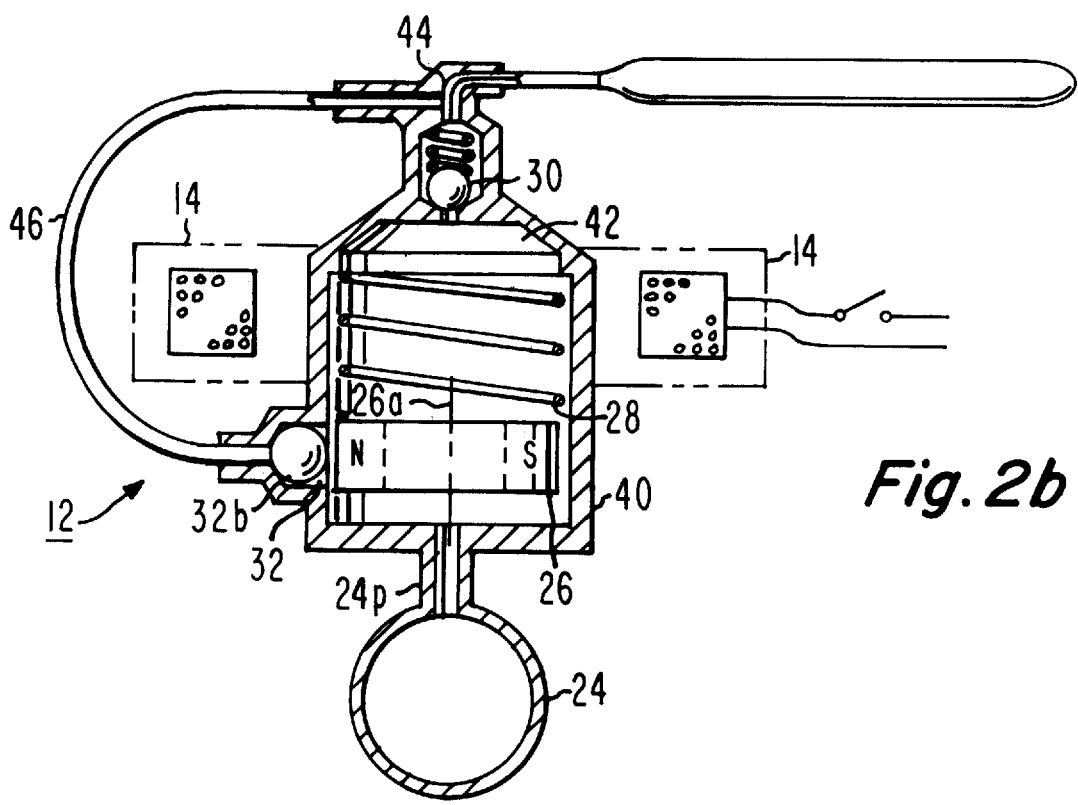
FIG. 2b is a similar diagram illustrating the rotor in a position representative of pressurizing a chamber of the prosthesis.
Figure 2C:
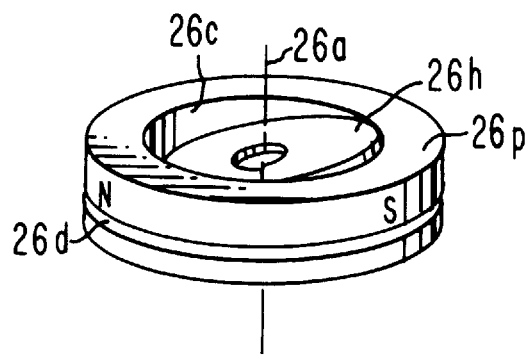
FIG. 2c is a simplified perspective or isometric view of a rotor which may be used in the arrangements of FIGS. 2a and 2b.
Figure 2D:
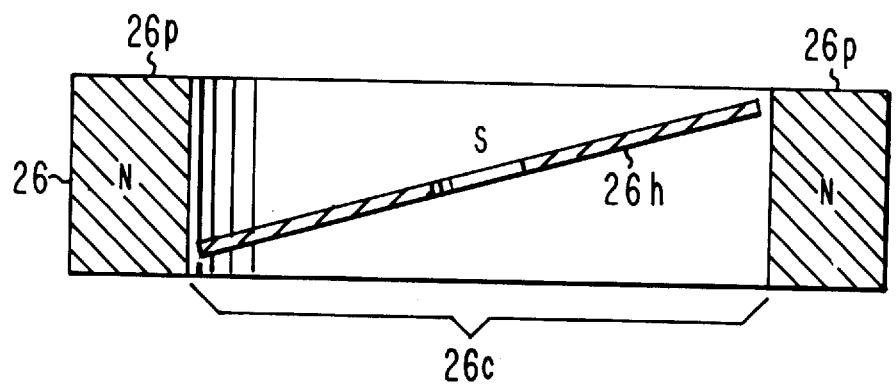
FIG. 2d is a simplified developed view of the interior of the rotor of FIG. 2c.

Pump 18 of FIG. 2a includes a nonmagnetic wall 40 defining a chamber 42 in which a magnetically active pump rotor 26 is located, with its rotational axis indicated as 26a. Pump rotor 26 is free to move axially within chamber 42, and is biased toward the position illustrated in FIG. 2a, which is a relatively distal position, by a spring illustrated as 28. Rotor 26, as illustrated in FIGS. 2c and 2d, has a peripheral portion 26p which is magnetized to define at least one pair of magnetic poles, designated N and S. The peripheral portion 26p of rotor 26 also defines a central aperture 26c, which contains a helically disposed vane. When rotor 26 rotates, the helical vane 26h spins, and acts as a pump, to tend to pump fluid from one side of the rotor to the other, or at least to pressurize the fluid on one side of the rotor. Thus, rotation of rotor 26 of FIG. 2a in a particular direction tends to move fluid from chamber 42 "upward" toward a check valve 30 at an outlet of the pump 18, thereby creating a fluid pressure which tends to open check valve 30, to allow fluid pressure to reach port 22 of chamber 20, to thereby inflate or pressurize the chamber.

Figure 3:
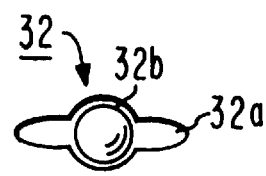
FIG. 3 illustrates the shape of an opening associated with a valve of the arrangements of FIGS. 2a and 2b.

So far not described in FIG. 2a is a further valve arrangement 32, which is illustrated as a ball valve, in which the ball 32b protrudes into the chamber 42. Valve arrangement 32 controls a fluid connection between fluid chamber 42 and a tee junction 44 communicating with fluid port 22 of chamber 20. More specifically, a tube or fluid path 46 is connected between tee junction 44 and valve 32. When valve 32 is open, which is to say when ball 32b protrudes into chamber 42, the fluid path is open, and any fluid pressure at tee junction 44 which is greater than the fluid pressure in the reservoir 24 allows flow of fluid from the tee junction and from chamber 20 back to reservoir 24. On the other hand, when ball 32b is flush with the wall 40 of chamber 42, fluid path 46 is closed, and pressure at tee junction 44 and in the chamber 20 cannot be relieved, so the chamber remains pressurized, and the penile prosthesis 12 maintains the penis 16 rigid. FIG. 3 illustrates a detail of the opening of valve arrangement 32 into chamber 42. AS illustrated in FIG. 3, the aperture is transversely elongated, so that fluid can escape around the ball 32b when the ball protrudes into the chamber 42.

As mentioned above, the rotor 26 of FIG. 2a preferably has at least one pair of opposed magnetic poles, designated N and S, associated with its outer surface. These magnetic poles N and S, during operation of the pump 18, interact with the rotating magnetic fields generated by rotary magnetic field generator 14, to cause the rotor to follow the rotation, and therefore to cause the rotor 26 to spin about axis 26a. When rotor 26 spins in a first direction, the helical vane 26h urges fluid toward check valve 30, thereby producing a fluid pressure which tends to overcome the spring pressure of the check valve, and to allow pressurization of the fluid at tee junction 44, at port 22, and in chamber 20, to render the chamber more rigid than in the unpressurized state, and to make the penis more rigid. The increase in pressure on the "upper side" of the rotating rotor due to having to overcome the spring pressure of check valve 30, and the forces generated by rotation of rotor 26, cause a opposing pressure and forces, which tend to drive the position of rotor 26 from the distal position illustrated in FIG. 2a toward the relatively proximal position illustrated in FIG. 2b. Thus, energization of rotary magnetic field generator 14 causes rotation in a first direction, which tends to drive pressurized fluid toward chamber 20, and which also tends to drive rotor 26 in a proximal direction. In its proximal position, the outer surface of rotor 26 pushes ball 32b of valve 32 flush with the walls 40 of chamber 42. With the ball 32b of valve 32 flush with the chamber wall, ball 32b closes off fluid path 46, which prevents pressure generated at junction 44 from being reduced by fluid discharge through path 46, through valve 32, back to reservoir 24. A detent in the side of rotor 26, illustrated as 26d in FIG. 2c, engages the ball 32b when rotor 26 is in its proximal position as a result of rotation in a direction which tends to pressurize chamber 20. Removal of the rotating magnetic field after the rotor has moved to the position illustrated in FIG. 2b stops the rotation of the rotor 26, and it no longer produces a pressure difference between its "upper" and "lower" sides. When rotor 26 stops rotating, check valve 30 closes, preventing fluid from returning to chamber 42 by way of the check valve 30. At the same time, the engaging of detent 26d by ball 32b prevents movement of rotor 26 under the influence of bias spring 28 away from the proximal position illustrated in FIG. 2b. Consequently, the rotor keeps ball 32b flush with the chamber wall, which maintains valve 32 in the closed condition. The closed condition of valve 32 prevents any reduction in the pressure at junction 44 and in the chamber 20 by way of path 46. Consequently, removal of the rotating magnetic field after a period of pump operation stops the pumping, but leaves the chamber pressurized or inflated, to maintain the penis in a rigid condition.

In order to remove the pressure from the chamber 20, to restore a flaccid condition of the penis, the rotary magnetic field is again applied, with the opposite direction of rotation. Reversal of the direction of rotation can be accomplished by adjustment of the control 14c of the generator, but a much easier way is simply to reverse the position of the rotary magnetic field generator 14 on the penis. Simply removing the magnetic field generator, turning it over, and reinserting the penis into the aperture 14a suffices to reverse the effective direction of rotation of the magnetic field which operates the rotor. The rotor consequently rotates in a direction opposite to the original direction of rotation, with the result that the rotor tends to produce greater pressure at its "bottom." The forces generated on the rotor when it rotates in a retrograde direction tend to drive the rotor axially upward as illustrated in FIG. 2b, which overcomes the detent force provided by ball 32b in detent 26d. With the detent force overcome, rotor 26 moves axially upward, releasing ball 32b. The pressure in path 46 causes ball 32b, when no longer held by the presence of the rotor in its lowermost position, to move so as to open valve 32. With valve 32 open, the pressure at junction 44 is relieved, and chamber 20 is depressurized. Depressurization of chamber 20 renders the penis flaccid.

Thus, the arrangement of FIGS. 1, 2a, 2b, 2c, 2d, and 3 renders the penis fitted with the prosthesis rigid when the rotary field generator is applied in one orientation, and renders the penis flaccid when the rotary field generator is applied in the other orientation.

Figure 4A:
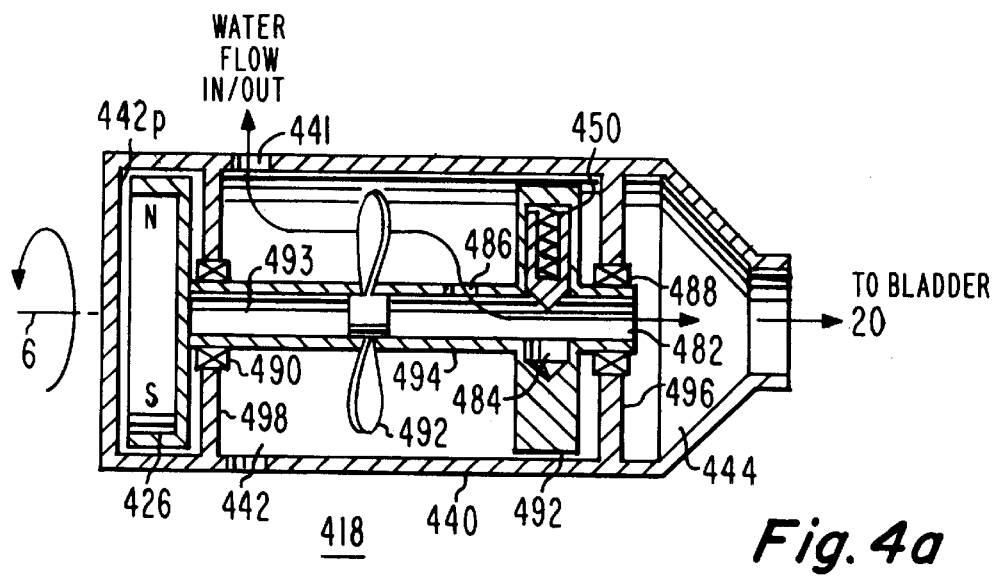
FIG. 4a is a simplified schematic representation of a portion of a pump and valve arrangement according to another aspect of the invention.
Figure 4B:
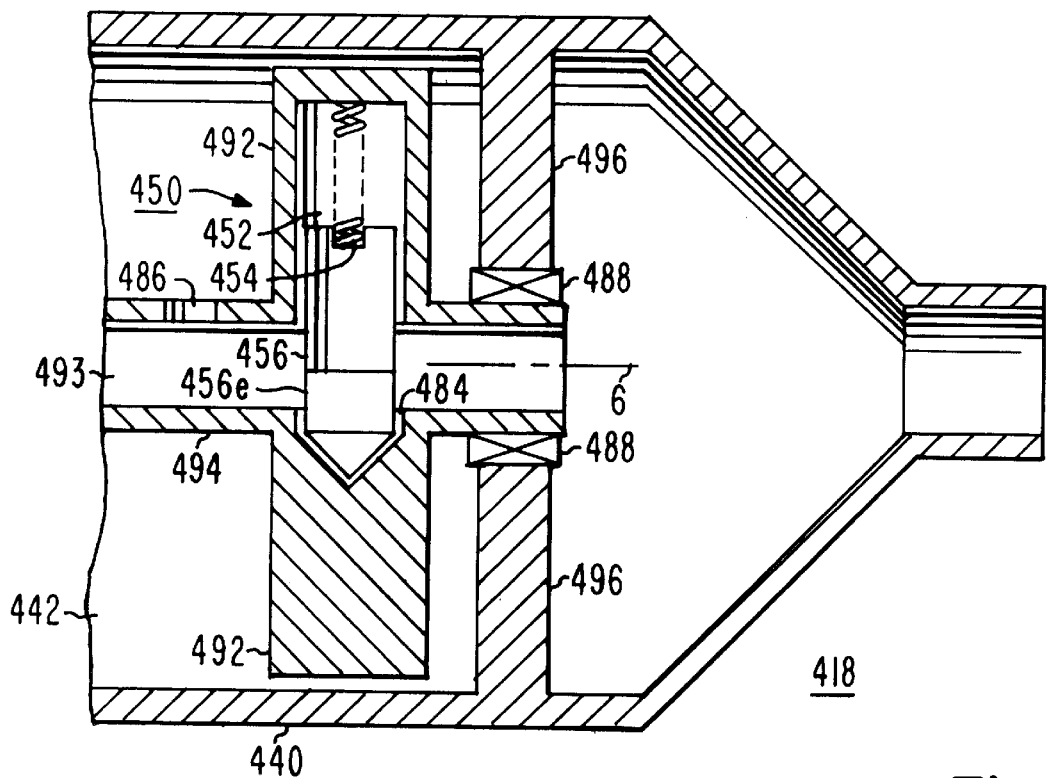
FIG. 4b is a detail thereof.

The spring pressure exerted on the ball of check valve 30 of FIG. 2a tends to cause a back pressure which must be overcome before the valve opens, so that the pressure at junction 44 may be less than the pressure which the rotor is capable of delivering. The arrangement of FIGS. 4a and 4b illustrates a pump 418 which is a substitute for pump 18 of FIGS. 2a and 2b, and which reduces the back pressure attributable to the biased check valve. Pump 418 includes a centrifugally operated valve arrangement 150 which is a substitute for the check valve 30 and valve 32 of FIGS. 2a and 2b. In FIG. 4a, the pump fluid chamber of pump 418 is designated 442, and the chamber walls are 440. The chamber wall 440 has at least one fluid port 441, which communicates with a fluid reservoir (not illustrated in FIG. 4a) corresponding to reservoir 24 of FIG. 1. The fluid chamber 442 is separated by a first wall 498 from an auxiliary proximal chamber 442p. The pump chamber is separated from a distal or outlet chamber 444 by a second wall 496. Chamber 444 communicates directly with fluid port 22 of chamber 20, without an additional check valve. The magnetically active rotor is illustrated as 426, which is located in proximal chamber 442p. Rotor 442p rotates on a hollow shaft 494 having an interior chamber 493, and is connected by shaft 494 to an impeller 492 and to a further rotary valve housing 492, both of which rotate in consonance with the magnetically active rotor 426. Rotor chamber 442p is sealed from fluid chamber 442 by a sealed bearing 490, and shaft 494 is supported by bearing 490 where the shaft passes through wall 498. The other end of shaft 494 is supported by a sealed bearing 488, which also acts to seal pump chamber 442 from outlet chamber 444.

The hollow shaft 494 of the arrangement of FIG. 4a has at least one slot or opening 486 located within pump chamber 442, so that fluid in the pump chamber can enter into the hollow interior of the shaft 494. Rotary valve housing 492 contains a valve aperture 484 which extends from the hollow interior 493 of shaft 494 to an outlet port 482 located in outlet chamber 444. Thus, when the magnetically active rotor 426 rotates under the influence of a rotating magnetic field, shaft 494 rotates, thereby rotating impeller or propeller 492, to thereby tend to produce pressure which tends to move fluid from fluid port 441 (from the reservoir, in other words) through the impeller 496, through the slot or aperture 486 in shaft 494, through the interior chamber 493 of shaft 494 to valve aperture 484, and through the valve aperture 484 to outlet aperture 482. Outlet aperture 482, as mentioned, corresponds directly with chamber 20, so that rotation in a first direction of the rotor 426 of FIG. 4*a* results in pressurization of the chamber, as in the arrangement of FIGS. 2*a* and 2*b*.

Rotary valve housing 492 of FIG. 4*a* contains a normally closed, centrifugally opened valve arrangement, illustrated in more detail in FIGS. 4*b*. In FIG. 4*b*, elements corresponding to those of FIG. 4*a* are designated by the same reference numerals. In FIG. 4*b*, the elements of centrifugal valve 450 include a cylindrical chamber 452 formed in valve housing 492, and a movable slug 454 fitted into the chamber 452 for movement therein in a radial direction relative to shaft axis 6. A spring 452 biases the slug toward the shaft 494. When the shaft 494 is not rotating, the slug is biased to the illustrated location, at which its presence seals off the through fluid path 484, so that, in effect, the shaft's central chamber 493 is sealed at the location of valve 450. This prevents flow of fluid either to or from the chamber 20, and thereby prevents depressurization of the chamber. Thus, no fluid can flow during those periods when the rotor 426 of FIG. 4*a* is not rotating, just as in the arrangement of FIGS. 2*a* and 2*b*. When rotor 426 of FIG. 4*a* rotates under the impetus of a rotating magnetic field, the shaft 494 and the valve housing 492 also rotate. When valve housing 492 rotates, slug 456 tends to be flung toward the exterior of the valve housing 492, so long as there is some mass eccentricity. A mass eccentricity can be guaranteed, and an improved seal provided, by making the inner end 456*e* (the end nearer to axis 6) of slug 456 from an elastomeric material, and the remainder from a heavier material, such as a dense metal. When the shaft 494 and the valve housing 492 rotate, therefore, the slug moves "upward" in FIG. 4*b*, withdrawing from the fluid path including portions 456 and 493, thereby opening the fluid path for the pumping of fluid. The valve 450 is opened by centrifugal force rather than by a pressure differential, so there is less pressure loss than in the arrangement of FIGS. 2*a* and 2*b*.

When the rotor of the pump rotates, the centrifugal closure opens and allows liquid to move from the reservoir to the chamber, or from the chamber to the reservoir, depending upon the rotational direction of the rotor. The rotational direction of the rotor is determined by the rotational direction of the rotating magnetic field, which, as mentioned, can be reversed simply by turning the magnetic field generator over. When the magnetic field is withdrawn, the pump rotor stops turning, and the centrifugal closure closes, keeping the chamber pressurized or depressurized, depending upon the previous action of the pump.

It should particularly be noted that the valve 450 of FIGS. 4*a* and 4*b* is closed whenever the rotor 426 does not rotate, and is opened by centrifugal forces when the rotor rotates in either direction. Thus, reversing the direction of pumping by reversal of the direction of the rotating magnetic fields has no effect on the operation of valve 450. Consequently, valve 450 takes the place of check valve 30 and of depressurizing valve 32 of FIGS. 2*a* and 2*b*.

Figure 5:
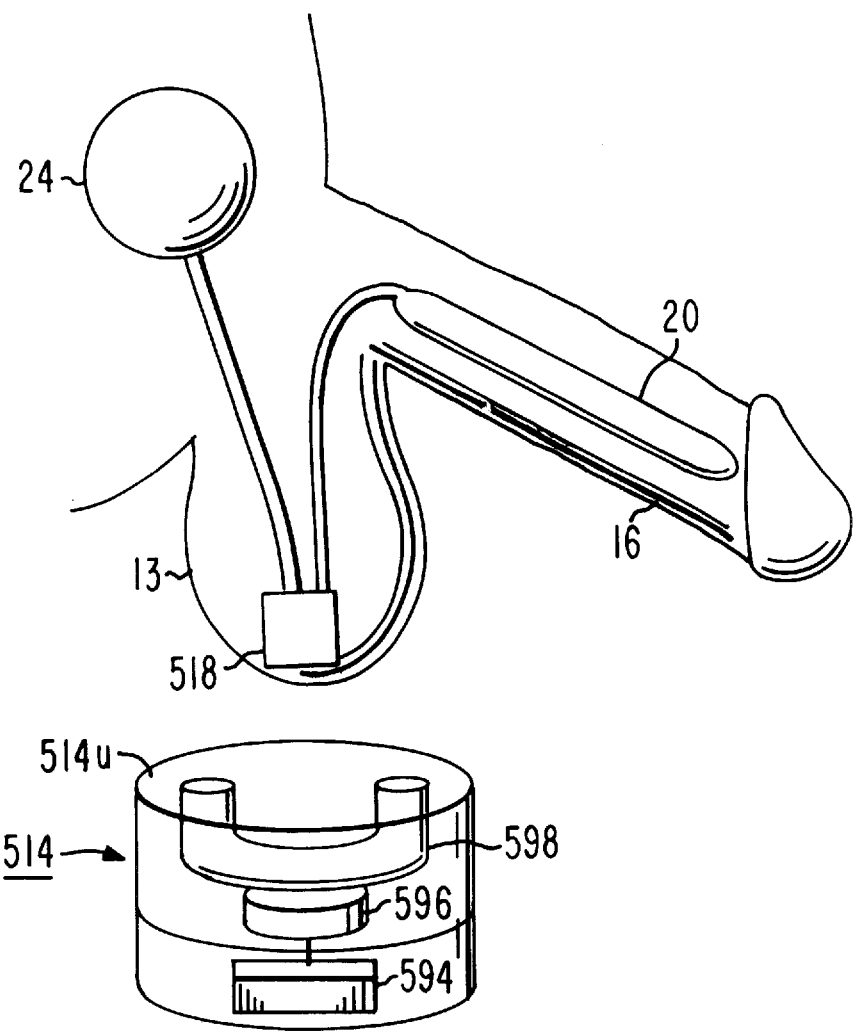
FIG. 5 is a simplified illustration of a multipiece prosthesis according to an aspect of the invention, in which the pump is located in the scrotum, and also illustrating a mechanically rotated magnetic field generator.

In FIG. 5, a pump-and-valve system 518 is illustrated as being located in scrotum 13, with tubes running to a reservoir 24 and to chamber 20 located in the penis 16. As illustrated in FIG. 5, the rotary magnetic field generator 514 includes a permanent magnet 598 driven by a rotary motor 596, which derives its control and power from a block illustrated as 594. Rotary magnetic field generator 514 produces a rotating field which extends toward the scrotum from the "upper" face 514*u* of generator 514. When upper face 514*u* is sufficiently close to the pump arrangement 518, the rotating magnetic field will drive the rotor (not illustrated in FIG. 5) of pump arrangement 518. The magnetic field strength of the magnet 598 should be sufficient, when upper surface 514*u* is close to, or in contact with, the skin of the scrotum, to rotate the pump.

Figure 6:
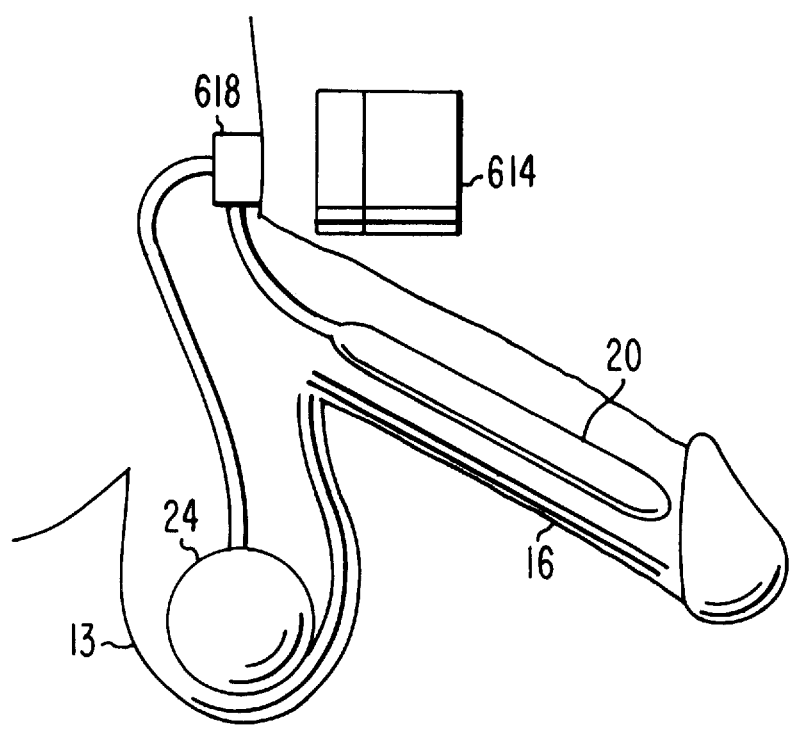
FIG. 6 illustrates another embodiment of the invention, in which the pump is located in the body above the penis, and the rotary magnetic field generator may be of any type.

FIG. 6 illustrates a somewhat different arrangement of the prosthesis in the body of a user. In FIG. 6, the pump and valve assembly is designated 614, and is located in the retropubic region. The reservoir 24 is placed elsewhere, in this case in the scrotum. In the illustrated location of the pump arrangement 618, the rotary magnetic field generator 614 is placed adjacent the pubic region, above the pump arrangement. As in the case of the other embodiments, the rotating magnetic field must be sufficiently strong to rotate the pump from the external location nearest the pump.

A penile prosthesis arrangement (10) according to an aspect of the invention comprises at least one pressurizable chamber (20) located in a distal portion (12*d*) of a prosthesis (12). In this context, the term "chamber" refers to an expansible or elastomeric container, or to a nondistensible bag, of whatever shape, and in whatever number. The chamber (20) includes a fluid port (22) by which fluid can enter and leave the chamber. The chamber (20) is located within the penis (16) of a patient for tending to make the penis (16) rigid in response to fluid pressure within the chamber (20), and to allow the penis (16) to be flaccid in the absence of significant fluid pressure in the chamber (20). The penile prosthesis arrangement (10) also includes a fluid reservoir (24), which may be located in the scrotum (13), or which is preferably located within a root portion (12*r*) of the prosthesis (12). A rotary pump (18) is coupled to the reservoir (24) and to the chamber (20). The rotary pump (18) includes a magnetically responsive rotor (26) adapted for rotation in the presence of a rotating magnetic field, for tending to pump fluid at least from the reservoir (24) toward the chamber (20) under the impetus of fluid pressure, to thereby pressurize the chamber (20) in response to operation of the pump (18). The penile prosthesis arrangement (10) also includes a generally annular magnetic field generator (14) defining a central aperture (14*a*) at least large enough to accommodate the penis (16) in the state in which the chamber (20) is pressurized. The magnetic field generator (14) generates a rotating magnetic field within and near the central aperture (14*a*). When the magnetic field generator (14) is placed over the penis by placing the central aperture (14*a*) around the penis (16) near its root (16*r*), the magnetically responsive rotor (26) rotates in response to the rotating magnetic field, to thereby tend to pressurize the chamber (20) and to render the penis (16) rigid.

The prosthesis arrangement may further include a controllable valve arrangement (30, 32, 450) operable in response to motion (or position as a result of motion) of the rotor (26) of the rotary pump (18), for tending to prevent depressurization of the chamber (20) when the rotating magnetic field no longer acts on the rotor (26). The controllable valve arrangement (30, 32, 450) may include a unidirectional check valve (30) located between the rotary pump (18) and the fluid port (22) of the chamber (20).

In one embodiment of the invention, the rotor (26) of the rotary pump (18) is free to move axially in response to the forces generated during rotation of the rotor (26), and the rotary pump (18) further includes a spring arrangement (28) coupled to the rotor (26), for tending to bias the rotor in a first axial direction (proximally) toward a first location (FIG. 2*b*), whereby, when the rotor (26) rotates for tending to pressurize the chamber (20), the forces acting on the rotor (26) tend to overcome the bias, and cause the rotor (26) to move in a second axial direction (distally) to a second position (FIG. 2a). In this embodiment, the controllable valve arrangement (30, 32, 450) comprises a mechanically actuable valve (32) which responds to the first (proximal) location of the rotor (26) for allowing depressurization of the chamber (20), and which responds to the second (distal) position of the rotor (26) to tend to prevent depressurization of the chamber (20). As a result, the chamber (20) tends to maintain pressure so long as the rotor is in the second (distal) position or location, and to be depressurized when the rotor (26) is near the first (proximal) location. In another embodiment, the valve arrangement (30, 32, 450) comprises at least one biased centrifugal closure (450) mounted for rotation with the rotor (426) for rotation therewith, for assuming a first condition (biased closed) when the rotor is stationary, and for assuming a second condition (open) when the rotor is rotating. The closure closes a fluid path (484) which is hydraulically in series with the rotary pump in the first condition, and opens the fluid path which is hydraulically in series with the rotary pump in the second condition, whereby when the pump is rotating the chamber can be pressurized, and when the pump is not rotating, the chamber tends to remain pressurized.

Other embodiments of the invention will be apparent to those skilled in the art. For example, the operating fluid of the may be liquids such as saline solution, or it may include gases such as nitrogen. The substance may not even be an actual fluid, but may be a fluid-like matter, such as a fine powder, so long as it has fluid-like characteristics. While the rotor 26 of the pump 18 has been described as having a helically disposed vane, it may have a plurality of such helical vanes, or it may have conventional impeller (propeller) blades, such as those found on a fan for moving air. It may be necessary to adjust the dynamic balance of the structure to achieve maximum rotational velocities, and in particular, the valve housing 492 of FIGS. 4a and 4b is inherently unbalanced in the illustrated arrangement, and will require some balance adjustment. One advantageous way to balance the valve 450 is to provide two movable slugs on opposite sides of the axis 6, each moving in opposition to the motion of the other in response to rotation. This may require selection of springs 452 having similar spring constants. While the pump and rotor of the pump have been illustrated and described as being located near the root of the penis, there is no particular reason to so limit the rotor location, and it may advantageously be placed in a relatively distal location, such as adjacent to, or even within, the glans penis, which location makes application of the rotational magnetic field generator simpler. While the pressure in the chamber or chambers of the prosthesis may be considered to be "constant" when the valves are closed to prevent fluid flow, valves may leak, and the pressure diminish over time; however, if the chamber pressure holds for as long as the user desires, the function of the prosthesis is accomplished.

What is claimed is:

1. A penile prosthesis system comprising:

at least one pressurizable chamber including a fluid port, said chamber adapted to be located within the penis of a patient for tending to make the penis rigid in response to fluid pressure within said chamber;

a fluid reservoir;

a rotary pump adapted to be implanted within the body of a user, said rotary pump being coupled to said reservoir and to said chamber, said rotary pump including a magnetically responsive rotor adapted for rotation in the presence of a rotating magnetic field, and an impeller for tending to pump fluid at least from said reservoir to said chamber under the impetus of fluid pressure, to thereby pressurize said chamber in response to operation of said pump; and a rotary magnetic field generator for generating a rotating magnetic field, for, when placed adjacent to the skin of said user at a location near said rotary pump, rotating said magnetically responsive rotor in response to said rotating magnetic field, to thereby tend to pressurize said chamber and to render the penis rigid;

controllable valve means operable in response to motion of said rotor of said rotary pump, for tending to prevent depressurization of said chamber when said rotating magnetic field no longer acts on said rotor, said controllable valve means comprising a unidirectional check valve located in the fluid path extending between said rotary pump and said port of said chamber.

2. A penile prosthesis system, comprising:

at least one pressurizable chamber including a fluid port, said chamber adapted to be located within the penis of a patient for tending to make the penis rigid in response to fluid pressure within said chamber;

a fluid reservoir;

a rotary pump adapted to be implanted within the body of a user, said rotary pump being coupled to said reservoir and to said chamber, said rotary pump including a magnetically responsive rotor adapted for rotation in the presence of a rotating magnetic field, and an impeller for tending to pump fluid at least from said reservoir to said chamber under the impetus of fluid pressure, to thereby pressurize said chamber in response to operation of said pump; and a rotary magnetic field generator for generating a rotating magnetic field, for, when placed adjacent to the skin of said user at a location near said rotary pump, rotating said magnetically responsive rotor in response to said rotating magnetic field, to thereby tend to pressurize said chamber and to render the penis rigid;

controllable valve means operable in response to motion of said rotor of said rotary pump, for tending to prevent depressurization of said chamber when said rotating magnetic field no longer acts on said rotor, wherein said rotor of said rotary pump is free to move axially in response to the forces generated during rotation of said rotor;

said rotary pump further comprising spring means coupled to said rotor, for tending to bias said rotor in a first axial direction toward a first location, wherein, when said rotor rotates for tending to pressurize said chamber, the forces acting on said rotor tend to overcome said bias, and cause said rotor to move in a second axial direction to a second position; and said controllable valve means comprises a mechanically actuable valve which responds to said first location of said rotor for allowing depressurization of said chamber, and which responds to said second position of said rotor to prevent depressurization of said chamber, wherein said chamber tends to maintain pressure so long as said rotor is in said second location, and to be depressurized when said rotor is near said first location.

3. A penile prosthesis system, comprising:

at least one pressurizable chamber including a fluid port, said chamber adapted to be located within the penis of a patient for tending to make the penis rigid in response to fluid pressure within said chamber;

a fluid reservoir;

a rotary pump adapted to be implanted within the body of a user, said rotary pump being coupled to said reservoir and to said chamber, said rotary pump including a magnetically responsive rotor adapted for rotation in the presence of a rotating magnetic field, and an impeller for tending to pump fluid at least from said reservoir to said chamber under the impetus of fluid pressure, to thereby pressurize said chamber in response to operation of said pump; and a rotary magnetic field generator for generating a rotating magnetic field, for, when placed adjacent to the skin of said user at a location near said rotary pump, rotating said magnetically responsive rotor in response to said rotating magnetic field, to thereby tend to pressurize said chamber and to render the penis rigid;

controllable valve means operable in response to motion of said rotor of said rotary pump, for tending to prevent depressurization of said chamber when said rotating magnetic field no longer acts on said rotor; wherein said valve means comprises at least one biased centrifugal closure mounted for rotation with said rotor, for assuming a first condition when said rotor is stationary, and for assuming a second condition when said rotor is rotating, said closure closing a fluid path hydraulically in series with said rotary pump in said first condition, and opening said fluid path hydraulically in series with said rotary pump in said second condition, wherein when said pump is rotating the pressure in said chamber can change, and when said pump is not rotating, said pressure in said chamber tends to remain constant.

4. A penile prosthesis system comprising:

at least one pressurizable chamber including a fluid port, said chamber adapted to be located within the penis of a patient for tending to make the penis rigid in response to fluid pressure within said chamber;

a fluid reservoir;

a rotary pump coupled to said reservoir and to said chamber, said rotary pump including a magnetically responsive rotor adapted for rotation in the presence of a rotating magnetic field, and an impeller for tending to pump fluid at least from said reservoir to said chamber under the impetus of fluid pressure, to thereby pressurize said chamber in response to operation of said pump;

a generally annular magnetic field generator defining a central aperture adapted to accommodate at least a portion of the penis when said chamber is pressurized, said magnetic field generator generating a rotating magnetic field within said central aperture, for, when said magnetic field generator is placed over the penis, rotating said magnetically responsive rotor in response to said rotating magnetic field, to thereby tend to pressurize said chamber and to render the penis rigid; and a check valve operable in response to motion of said rotor coupled to said rotary pump and to said pressurizable chamber, for providing a path for easy flow of said fluid from said rotary pump to said pressurizable chamber, and to block flow from said pressurizable chamber to said rotary pump.

5. An apparatus for reshaping a portion of a body, said apparatus comprising:

a fluid reservoir adapted to be placed in the body at a concealed location;

a chamber located near the portion of the body to be reshaped;

a rotary pump adapted to be implanted within the body of a user, said rotary pump being coupled to said reservoir and to said chamber, said rotary pump including a magnetically responsive rotor adapted for rotation in the presence of a rotating magnetic field, and an impeller for tending to pump fluid at least from said reservoir to said chamber under the impetus of fluid pressure, to thereby pressurize said chamber in response to operation of said pump;

a rotary magnetic field generator for generating a rotating magnetic field, for, when placed adjacent to the skin of said user at a location near said rotary pump, rotating said magnetically responsive rotor in response to said rotating magnetic field, to thereby tend to pressurize said chamber and to reshape the portion of the body;

controllable valve means operable in response to motion of said rotor of said rotary pump, for tending to prevent depressurization of said chamber when said rotating magnetic field no longer acts on said rotor, wherein said controllable valve means comprises a unidirectional check valve located between said rotary pump and said port of said chamber.

* * * * *